United States Patent
Toso et al.

(10) Patent No.: US 7,985,175 B2
(45) Date of Patent: Jul. 26, 2011

(54) PELVIC FLOOR REPAIR IMPLANTS AND METHODS

(75) Inventors: Kenneth E. Toso, Westborough, MA (US); Doreen Rao, Sudbury, MA (US)

(73) Assignee: Boston Scientific Scimed, Inc., Boston, MA (US)

(*) Notice: Subject to any disclaimer, the term of this patent is extended or adjusted under 35 U.S.C. 154(b) by 228 days.

(21) Appl. No.: 11/906,913

(22) Filed: Oct. 3, 2007

(65) Prior Publication Data

US 2008/0081945 A1    Apr. 3, 2008

Related U.S. Application Data (60) Provisional application No. 60/849,320, filed on Oct. 3, 2006.

(51) Int. Cl.
*A61F 2/00* (2006.01)
(52) U.S. Cl. .......................................................... 600/37
(58) Field of Classification Search ............. 600/29–32, 600/37; 606/151; 623/23.65
See application file for complete search history.

(56) References Cited

U.S. PATENT DOCUMENTS

| | | | |
|---|---|---|---|
| 5,840,011 | A | 11/1998 | Landgrebe et al. |
| 6,042,534 | A | 3/2000 | Gellman et al. |
| 6,197,036 | B1 | 3/2001 | Tripp et al. |
| 6,808,487 | B2 | 10/2004 | Migliari |
| 6,960,160 | B2 | 11/2005 | Browning |
| 7,229,404 | B2 * | 6/2007 | Bouffier .......................... 600/30 |
| 2002/0007222 | A1 | 1/2002 | Desai |
| 2003/0191360 | A1 | 10/2003 | Browning |
| 2004/0039453 | A1 | 2/2004 | Anderson et al. |
| 2004/0267088 | A1 | 12/2004 | Kammerer |
| 2005/0070829 | A1 | 3/2005 | Therin et al. |

FOREIGN PATENT DOCUMENTS

| | | |
|---|---|---|
| WO | WO-90/14795 | 12/1990 |
| WO | WO-98/35632 | 8/1998 |
| WO | WO-02/30293 | 4/2002 |

* cited by examiner

*Primary Examiner* — Charles A Marmor, II
*Assistant Examiner* — Christine D Hopkins
(74) *Attorney, Agent, or Firm* — Bingham McCutchen LLP (57) ABSTRACT

The invention generally relates to surgically implantable supportive slings. More specifically, in various embodiments, the invention is directed to sling assemblies for pelvic floor repair that utilize one or more materials, attached without a mechanical fixation device, and related methods of use and fabrication.

22 Claims, 7 Drawing Sheets

PELVIC FLOOR REPAIR IMPLANTS AND METHODS

RELATED APPLICATIONS

This application claims the benefit of U.S. Provisional Application Ser. No. 60/849,320, filed Oct. 3, 2006 and titled "Pelvic Floor Repair Implants and Methods," the entire contents of which are incorporated herein by reference.

BACKGROUND

Urinary incontinence affects over 13 million men and women of all ages in the United States. Stress urinary incontinence (SUI) affects primarily women and is generally caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. Moreover, the condition of stress urinary incontinence is often compounded by the presence of untreated vaginal vault prolapse or other more serious pelvic floor disorders. Often, treatments of stress incontinence are made without treating the pelvic floor disorders, potentially leading to an early recurrence of the pelvic floor disorder.

Pelvic floor disorders are often treated using an implantable supportive sling. Such slings may be made from a variety of materials, and often incorporate two different types of material connected via mechanical fixation devices, such as staples and sutures. When one of the materials is a biologic material, the surgeon must suture the two materials together, a labor-intensive and time-consuming process. Eliminating the need for fixation devices and the need for suturing can reduce costs for producing and utilizing implantable slings.

SUMMARY OF THE INVENTION

The invention addresses the deficiencies of the prior art by providing an improved implantable sling assembly for supporting an anatomical site in the body of a patient. More particularly, in various aspects, the invention provides a supportive sling assembly formed without a mechanical fixation device, along with methods of making and using such a sling assembly.

In one aspect, the invention provides a sling assembly adapted to be implanted into a patient for the treatment of pelvic floor disorders such as cystocele, rectocele, vaginal prolapse, and other similar disorders. The implantable sling assembly includes a sling having at least one through-aperture, and at least a first support arm having first and second ends. The support arm optionally also includes at least one through-aperture on the first end. The second end of the support arm is adapted to fit through the through-aperture of the sling and, when applicable, through the through-aperture of the first end of the support arm to secure the support arm to the sling.

According to various embodiments, the sling is configured in any suitable shape, including, for example, square, rectangular, trapezoidal, quadrilateral, triangular, circular, elliptical, or polygonal. The sling may have a plurality of through-apertures located in any suitable location on the sling.

In one embodiment, the through-aperture of the sling includes a slot, a loop, a ring, or any other suitable support mechanism that provides structural support for the through-aperture. When used, the support mechanism is attached to a portion of the sling or inserted within the sling.

In some embodiments, the sling assembly includes a plurality of support arms with each support arm having one or more corresponding sling through-apertures, each sling through-aperture has a corresponding support arm. A plurality of support arms may be adapted to interfit with a single sling through-aperture.

The sling assembly may also include at least one anchor attached to the at least one support arm. The anchor may be attached to the at least one support arm before or after the support arm is attached to the sling. In certain embodiments, the sling assembly includes a plurality of support arms and a plurality of anchors, with an anchor attached to one or more of the support arms. According to one implementation, upon implantation of a sling assembly in a patient, an anchor is positioned at a suitable location in the periurethral tissues of the patient.

The sling assembly may also include a fastener adapted to attach the first end of the support arm to a central portion of the support arm after the support arm is secured to the sling. The fastener may also attach the support arm to the sling.

According to various embodiments, the sling and the support arms are made from any suitable biologic or synthetic material. The sling may be a knitted mesh sling or a woven sling. The at least one support arm may be a mesh or woven arm or an elastic member.

According to a further aspect, the invention provides various methods for manufacturing a sling implant, and various methods for delivering an implant, such as a sling or sling assembly, to an anatomical site in the body of a patient. The methods of delivery include, without limitation, trans-obturatural, suprapubic, prepubic, and transvaginal approaches.

Other aspects and advantages of the invention are described below with respect to various illustrative embodiments.

BRIEF DESCRIPTION OF THE DRAWINGS

Various illustrative embodiments of the invention are described below with reference to the appended drawings, which may not be drawn to scale and in which like parts are designated by like reference designations. These depicted embodiments are to be understood as illustrative of the invention and not as limiting in any way.

DESCRIPTION OF ILLUSTRATIVE EMBODIMENTS

As described in summary above, in various illustrative embodiments, the invention is directed to an implantable sling formed from a core material and at least one arm attached to the core without the use of a mechanical fixation device.

Figure 1A:
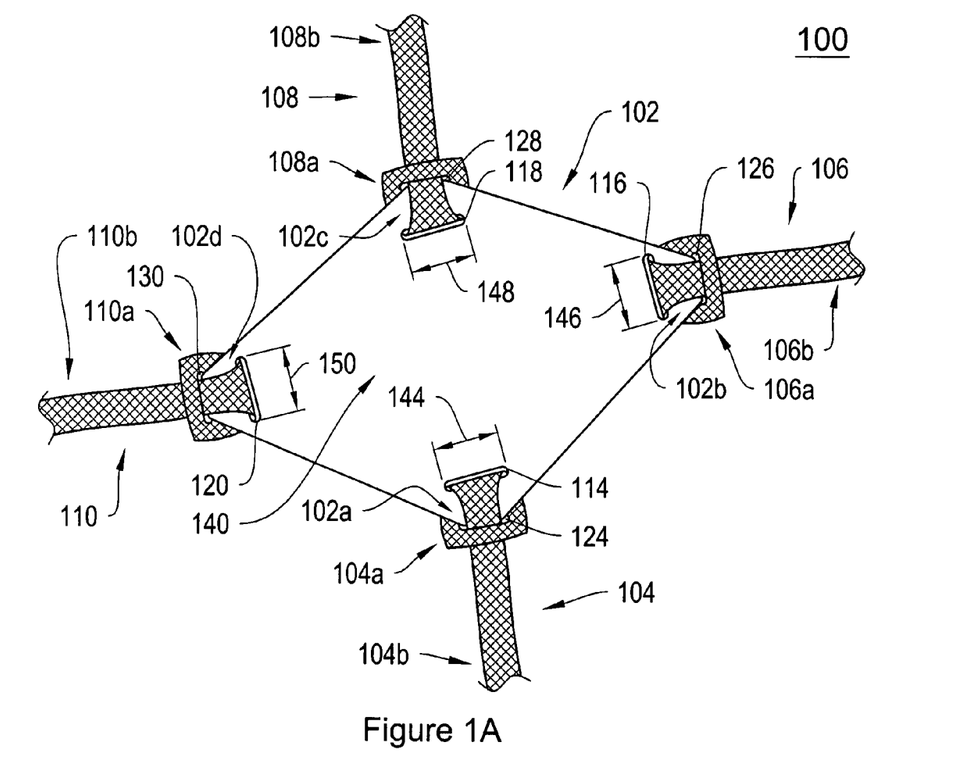
FIG. 1A is a top view of an exemplary sling assembly employing a sling and four support arms.

FIG. 1A is a top view of an exemplary sling assembly 100 employing a sling 102 and first 104, second 106, third 108, and fourth 110 support arms according to an illustrative embodiment of the invention. The sling 102 includes first 114, second 116, third 118, and fourth 120 slots, each of the slots 114, 116, 118, and 120 having a width 144, 146, 148, and 150, respectively. According to one feature, the sling 102 is substantially rectangular, and the slots 114, 116, 118, and 120 are positioned approximately in the corners 102a-102d of the sling 102. However, the slots 114, 116, 118, and 120 may be positioned in any suitable location on the sling 102, and the sling 102 may be any suitable shape including polygonal and elliptical, as discussed, for example, below with regard to FIGS. 2A-2C.

The support arms 104, 106, 108, and 110 are each threaded through a corresponding slot 114, 116, 118, and 120 in the sling 102, as described in further detail below. While the illustrative sling assembly 100 includes a sling 102 with four slots 114, 116, 118, and 120, and four corresponding support arms 104, 106, 108, and 110, according to alternative embodiments, the sling 102 may have any number of slots having any number of support arms. Optionally, a plurality of support arms, such as two or more of arms 104, 106, 108, and 110 may be adapted to interfit with a single slot on the sling 102 by threading the plurality of support arms through the slot as described below.

Figure 1B:
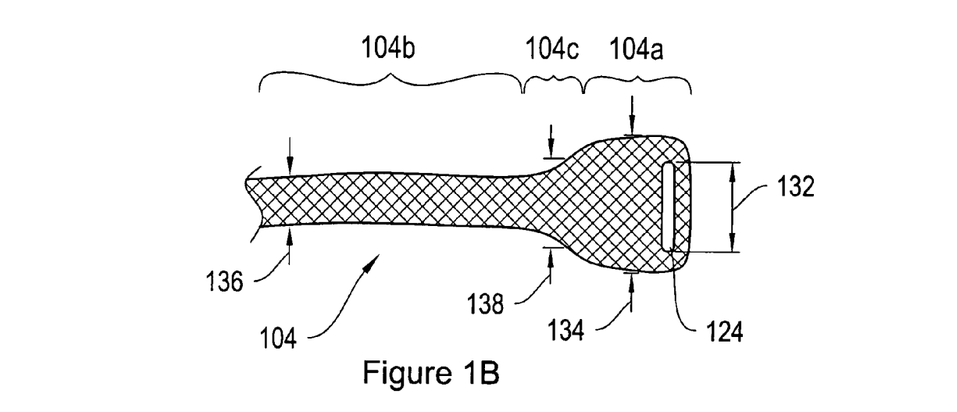
FIG. 1B is a top view of one of the support arms of FIG. 1A.

FIG. 1B depicts a top view of an exemplary support arm 104. The support arm 104 includes a first end 104a, a second end 104b, a middle portion 104c, and an aperture 124. According to one illustrative feature, the first end 104a of the support arm 104 has a width 134 that is greater than the width 144 of the slot 114 of FIG. 1A, which is greater than the width 136 of the second end 104b of the support arm 104. The middle portion 104c has a width 138 that tapers from the width 134 of the first end 104a to the width 136 of the second end 104b. However, according to alternative embodiments, the arm 104 may be configured without a tapered middle portion 104c. According to further embodiments, the arm 104 may be configured to have a uniform width.

According to the illustrative embodiment, the aperture 124 is located in the first end 104a of the support arm 104. The aperture 124 has a width 132 that is slightly larger than the width 136 of the second end 104b of the support arm 104.

In operation, the sling assembly 100 is assembled as the arms 104-110 are inserted through the applicable apertures 114-120, respectively. To illustrate the assembly of arm 104, in a first step, a portion of the second end 104b of the support arm 104 is threaded through the slot 114 from the bottom surface (not shown) toward the top surface 140 of the sling 102, while the first end 104a of the support arm 104 remains underneath the sling 102. In a second step, the first 104a and second 104b ends of the support arm 104 are then folded back toward the edge of the sling 102, and the second end 104b of the support arm 104 is threaded through the aperture 124 in the first end 104a of the arm 104 to secure the support arm 104 to the sling 102. According to one feature, the support arms 106, 108, and 110 are threaded through the slots 116, 118, and 120, respectively, and looped through apertures 126, 128, and 130, respectively, in substantially the same manner as the support arm 104, with respect to the slot 114.

Figure 2A:
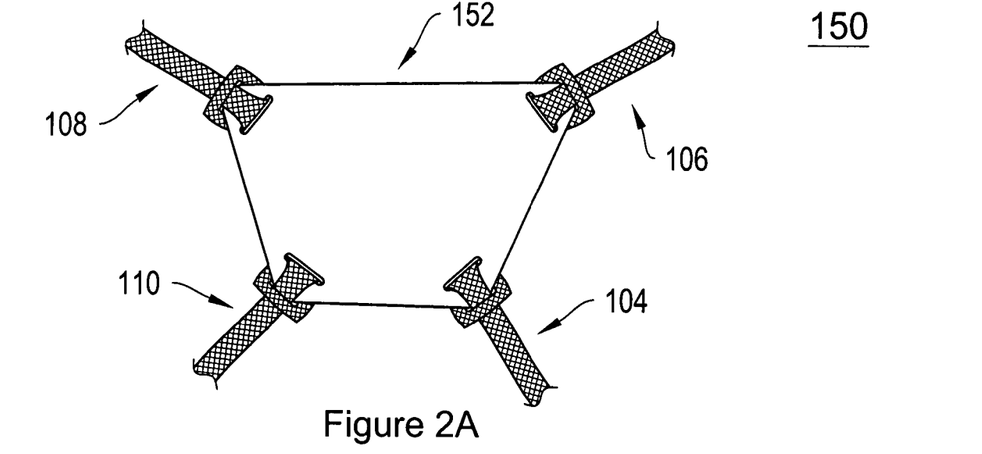
FIG. 2A is a top view of an alternative exemplary sling assembly employing a sling and four support arms.
Figure 2B:
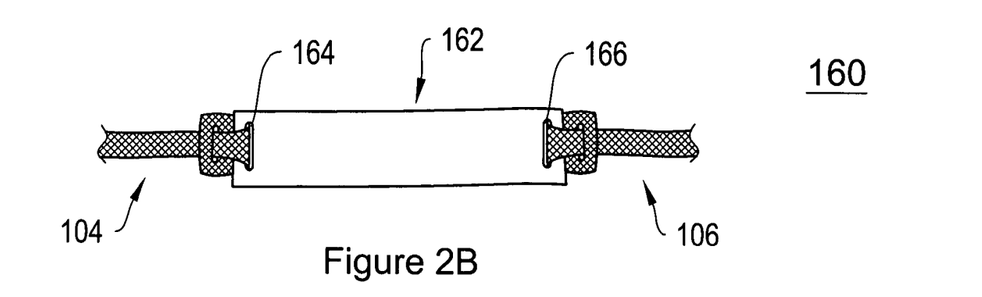
FIG. 2B is a top view of an exemplary sling assembly employing a sling and two support arms.
Figure 2C:
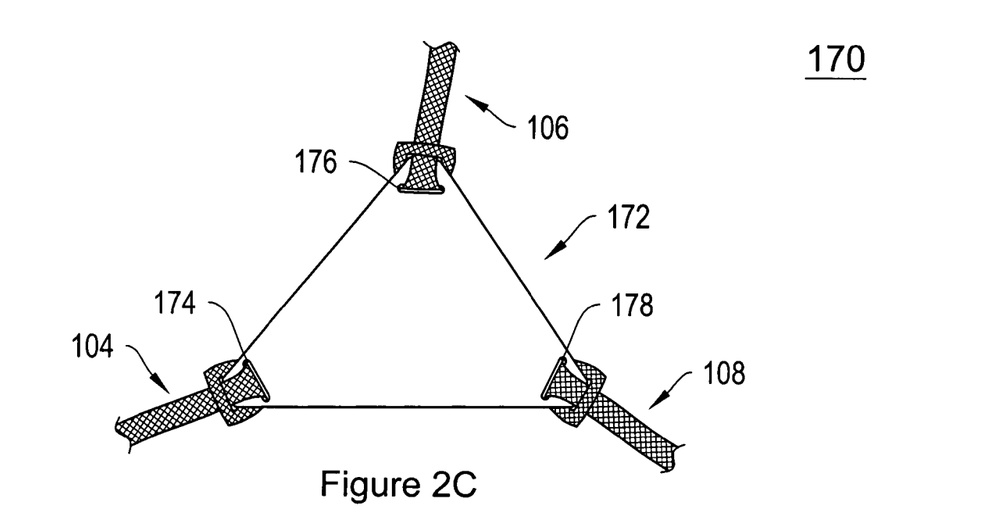
FIG. 2C is a top view of an exemplary sling assembly employing a sling and three support arms.

While the sling 102 is substantially rectangular, as shown in FIG. 1A, the sling 102 may be configured in any suitable shape. FIG. 2A-2C illustrate various alternative exemplary configurations. FIG. 2A is a top view of an alternative exemplary sling assembly 150 employing a trapezoidal sling 152 with four support arms 104, 106, 108, and 110. FIG. 2B is a top view of an exemplary sling assembly 160 employing a long rectangular sling 162 and two support arms 104 and 106. The sling 162 includes two slots 164 and 166 adapted to interfit with the support arms 104 and 106, respectively. FIG. 2C is a top view of an exemplary sling assembly 170 employing a triangular sling 172 and three support arms 104, 106, and 108. The sling 172 includes three slots 174, 176, and 178.

According to one illustrative feature, the sling 102 is between about 2 cm and 15 cm wide, and between about 5 cm and about 15 cm long. Each of one or more exemplary slots included in the sling 102 are between about 0.5 cm and about 5 cm wide. According to another illustrative feature, the one or more support arms used with the sling are between about 5 cm and 20 cm long, and have first ends between about 0.5 cm wide and about 5 cm wide with one or more apertures between about 0.1 cm wide and about 4 cm wide, and second ends between about 0.5 cm wide and about 3 cm wide.

Tangs are the frayed edges that result from cutting, chopping, tearing, fraying, or otherwise shaping a mesh material. According to one embodiment, the sling 102 is tanged, while in other implementations, the sling is constructed of a detanged mesh material. A detanged mesh material may be formed by smoothing, rounding, or removing the tangs from the material.

Figure 3A:
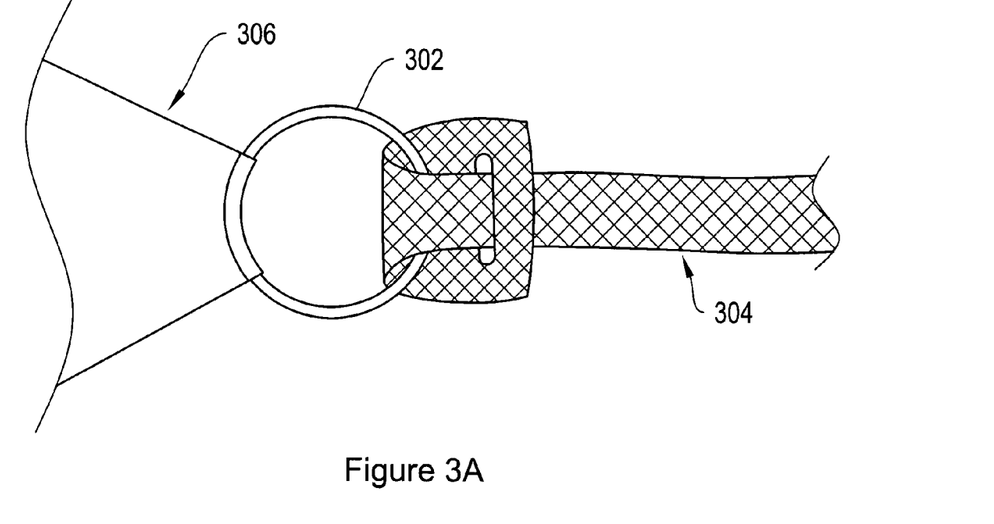
FIG. 3A is a top view of an exemplary sling support arm through-aperture.
Figure 3B:
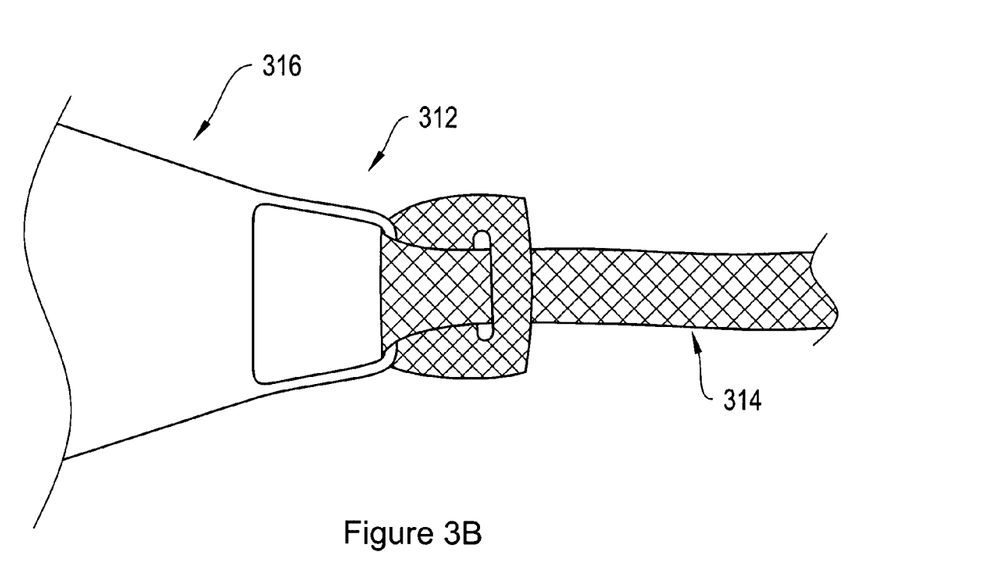
FIG. 3B is a top view of an alternative exemplary sling support arm through-aperture.

FIGS. 3A and 3B illustrate alternative sling through-apertures 302 and 312 for attaching support arms 304 and 314. In FIG. 3A, the through-aperture is a ring 302. The ring 302 is attached to the sling 306, and the support arm 304 is attached to the ring 302. While in FIG. 3A, the ring 302 is attached to the sling 306 along only a portion of its perimeter, in other embodiments, the ring 302 may be placed completely within the sling 306. According to one feature, the ring 302 provides structural support to the through-aperture. In FIG. 3B, the through-aperture is a loop 312 attached to the sling 306, and the support arm 314 is attached to the loop 312.

Figure 4A:
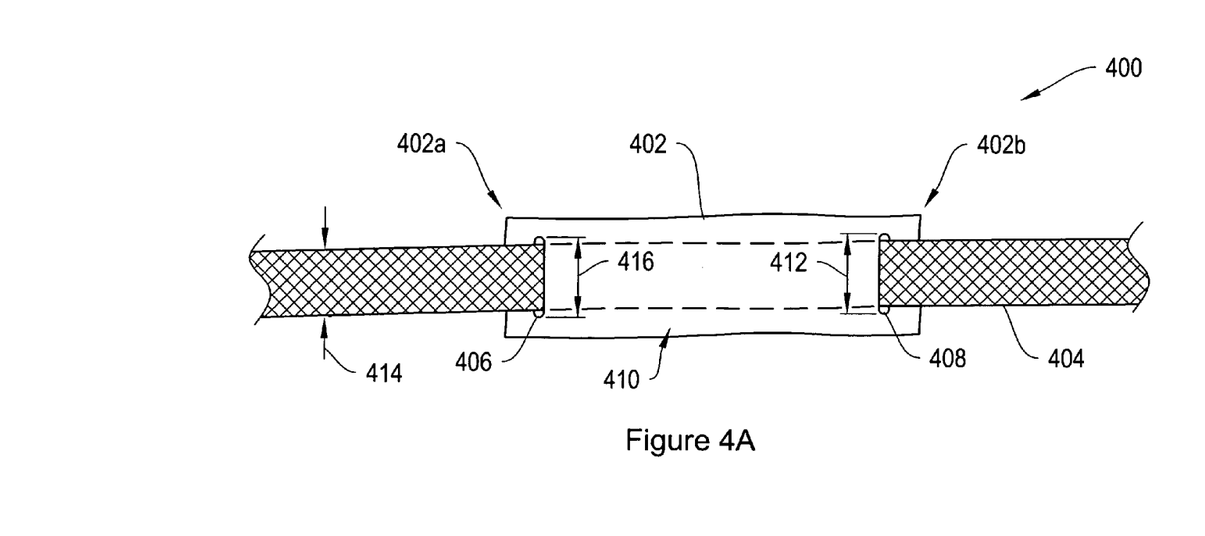
FIG. 4A is a top view an exemplary sling assembly employing a sling and one support arm threaded through the sling.
Figure 4B:
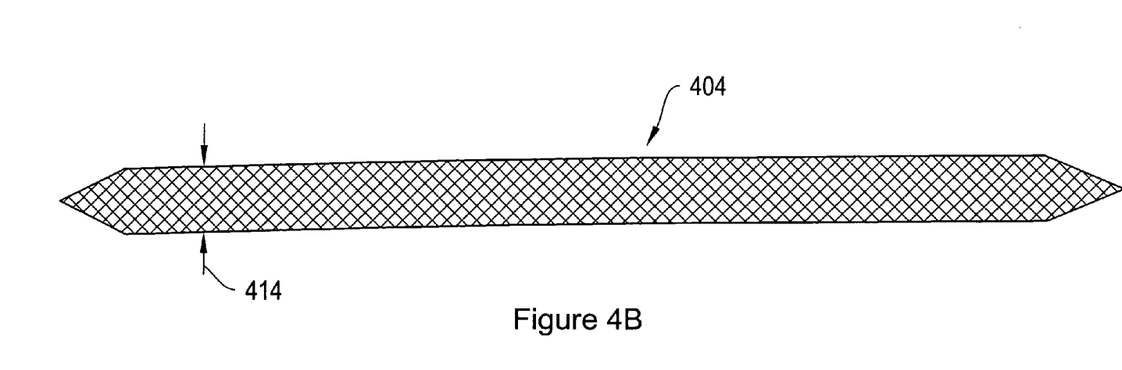
FIG. 4B is a top view of the support arm of FIG. 4A.

FIGS. 4A and 4B illustrate an exemplary alternative embodiment of a sling assembly 400 employing a sling 402 and a support arm 404 threaded through the sling 402, without the use of slots within the support arms. As shown in FIG. 3A, the sling 402 includes first 406 and second 408 slots, with each slot 406 and 408 having a width 416 and 412, respectively. According to one feature, the width 416 of the first slot 406 is substantially equal to the width 412 of the second slot 408. According to another feature, the sling 402 is substantially rectangular, and the slots 406 and 408 are positioned near the ends 402a and 402b of the sling. However, the slots 406 and 408 may be positioned in any suitable location on the sling 402, and the sling 402 may be any suitable shape, including polygonal and elliptical. According to the illustrative embodiment, the support arm 404 is threaded from a top side 410 of the sling 402 through the first slot 406 to the bottom side (not shown) of the sling 402, extends underneath the sling 402, and is then threaded back through the second slot 408 to the top side 410 of the sling 402. While the sling assembly 400 includes a sling 402 with two slots 406 and 408, in alternative embodiments the sling assembly 400 includes a sling 402 with any number of slots, such as slots 406 and 408, with the support arm 404 woven through the slots along the sling 402, similar to the weaving shown through slots 406 and 408.

As shown in FIG. 4B, the support arm 404 has a substantially uniform width 414. According to one feature, the width 414 of the support arm 404 is less than the width 416 of the first slot 406 and the width 412 of the second slot 408.

Figure 5:
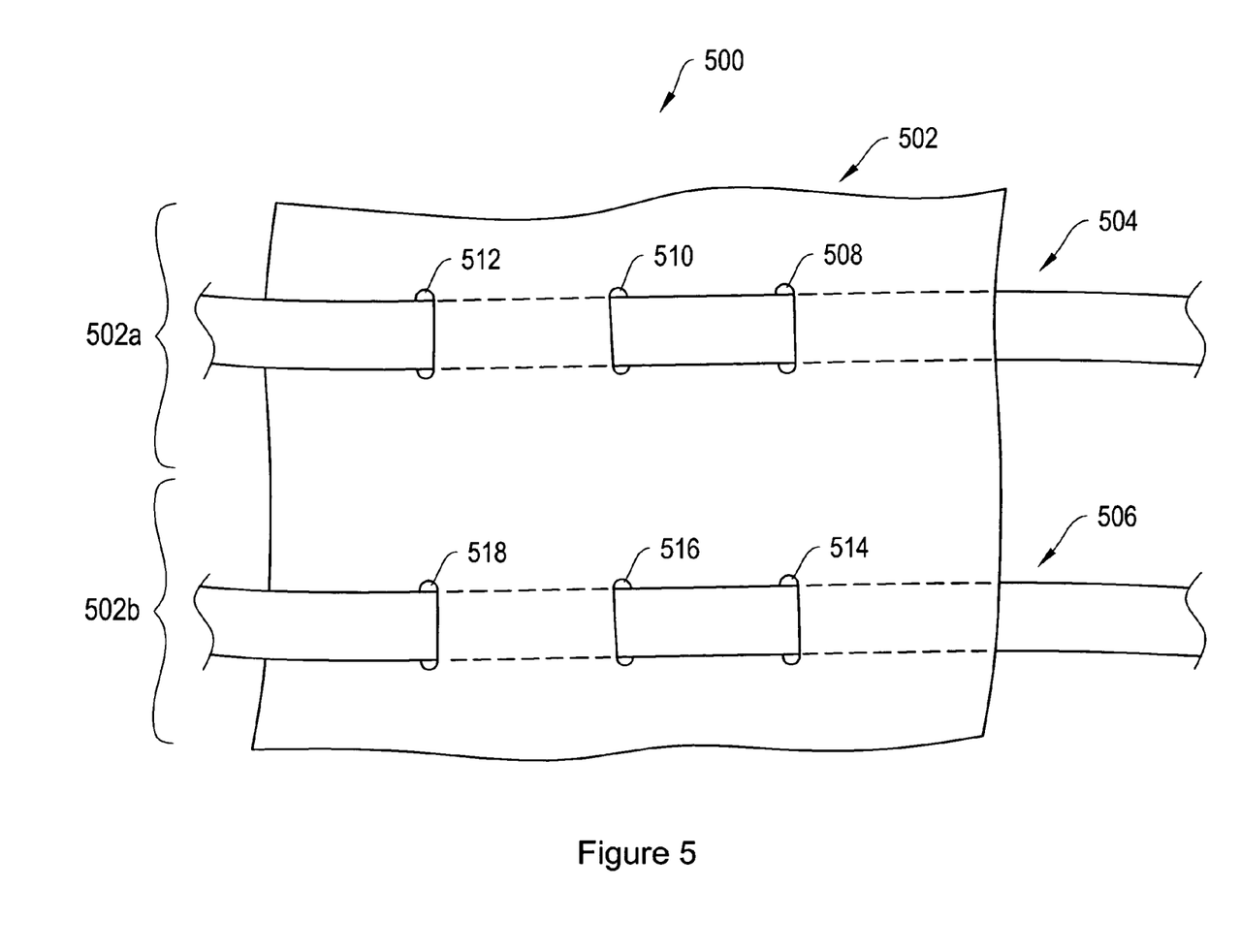
FIG. 5 is a top view of another exemplary sling assembly employing a sling and two support arms threaded through the sling.
Figure 6A:
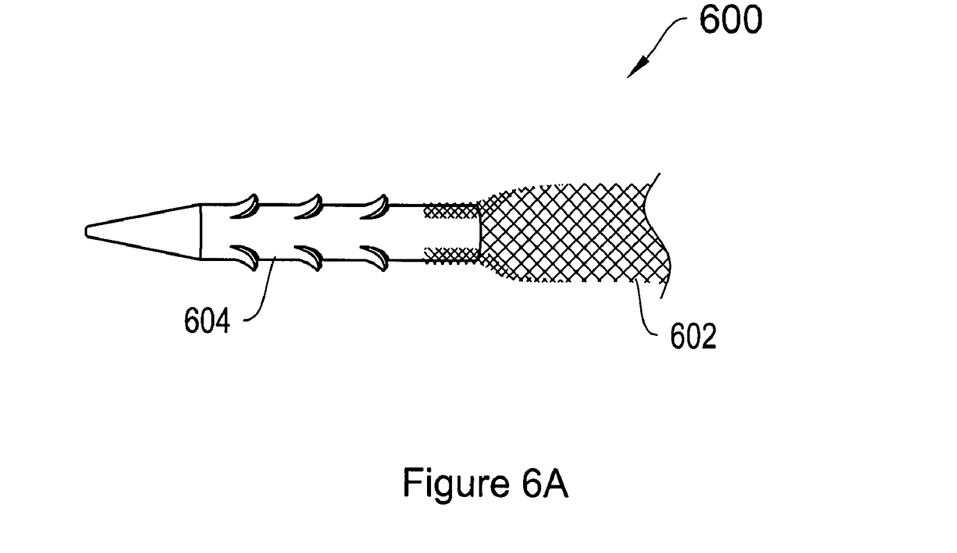
FIGS. 6A-6D depict anchors with attached support arms.
Figure 6B:
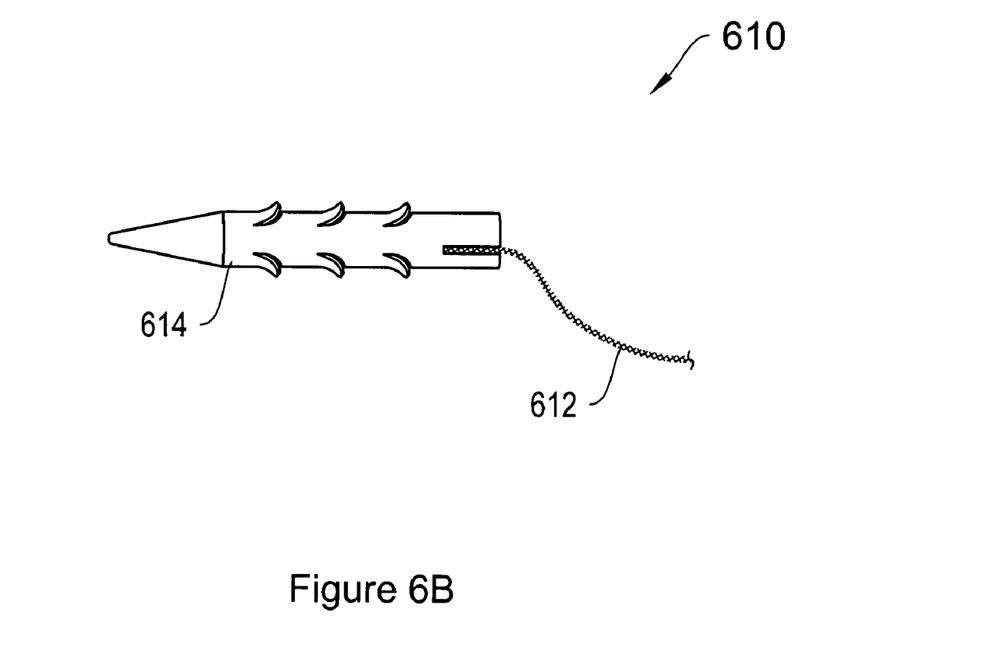
Figure 6C:
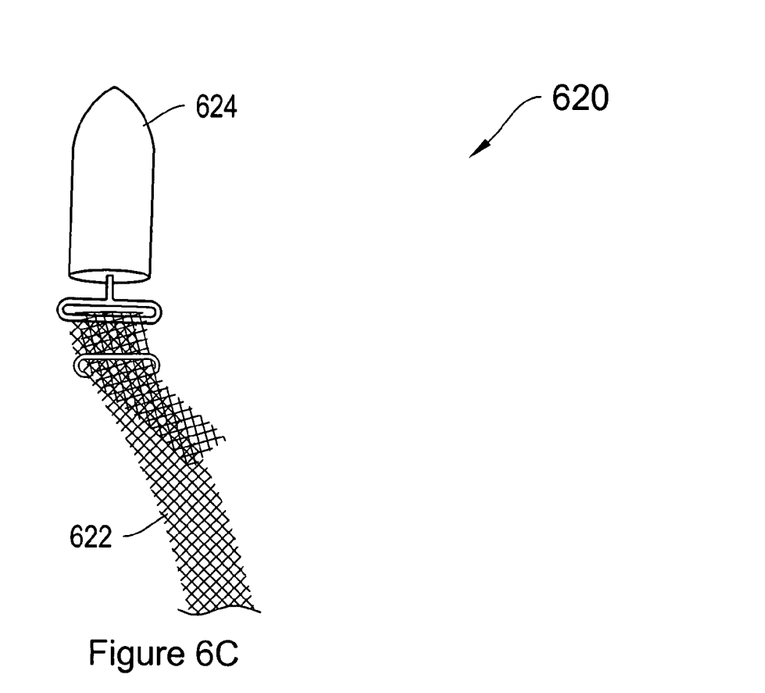
Figure 6D:
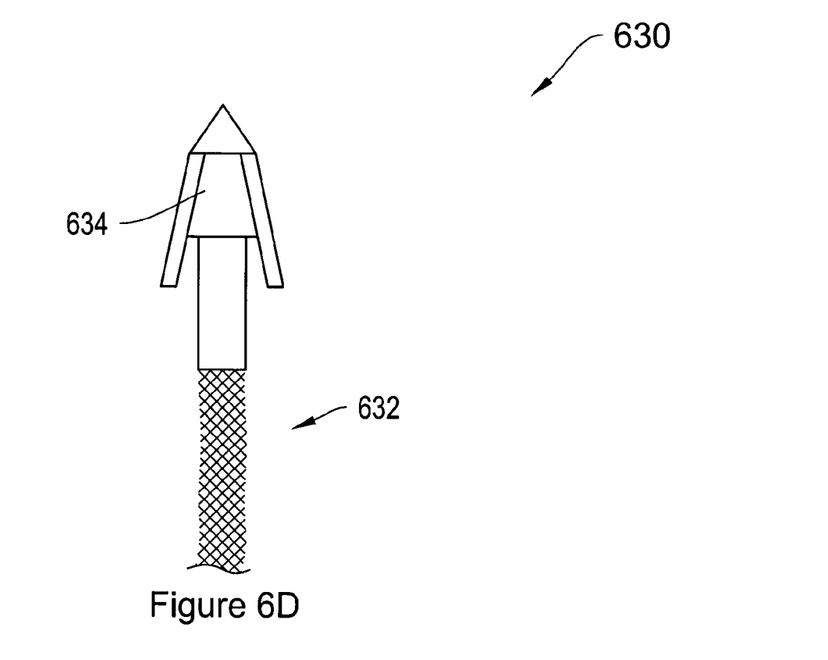

FIG. 5 is a top view of another exemplary sling assembly 500 employing a sling 502 and first 504 and second 506 support arms threaded through the sling 502. The sling 502 is substantially rectangular and includes six slots 508, 510, 512, 514, 516, and 518. According to one feature, the slots 508, 510, 512, 514, 516, and 518 have widths substantially similar to the slots 206 and 208 of FIG. 2A. According to one illustrative embodiment, the first three slots 508, 510, and 512 are positioned substantially parallel to each other, spaced along a top portion 502a of the sling 502, and positioned so as to receive the support arm 504. The next three slots 514, 516, and 518 are also positioned substantially parallel to each other and spaced along a bottom portion 502b of the sling 502 and positioned so as to receive the support arm 506. In operation, the first support arm 504 is interwoven through the slots 508, 510, and 512 by being threaded up through slot 508, down through slot 510, and up through slot 512. Similarly, the second support arm 506 is threaded up through slot 514, down through slot 516, and back up through slot 518.

The slots 508, 510, 512, 514, 516, and 518 may be positioned in any suitable location on the sling 502, and the sling 502 may be any suitable shape, including polygonal and elliptical. While the sling 502 includes six slots 508, 510, 512, 514, 516, and 518, the sling 502 may alternatively be configured with any number of slots. Additionally, while the sling assembly 500 includes two support arms 504 and 506, according to alternative embodiments, the sling assembly 500 may include any number of support arms configured to interweave through one or more slots along the sling 502.

FIGS. 6A-6D depict exemplary anchor assemblies 600, 610, 620, and 630 including anchors 604, 614, 624, and 634 with attached support arms 602, 612, 622, and 632, as described in U.S. patent applications U.S. Ser. No. 11/152898 entitled "Systems, Methods and Devices Relating to Implantable Supportive Slings" and U.S. Ser. No. 10/147533 entitled "Bone Anchor Implantation Device," the entire contents of which are incorporated herein by reference. According to one embodiment, anchors 604, 614, and 624 are soft tissue anchors, while anchor 634 is a bone anchor.

Exemplary mesh materials that may be used for the slings and, as applicable, any of the support arms include, for example, synthetic materials, natural materials (e.g., biological) or a combination thereof. In certain embodiments, the mesh is woven. In certain embodiments, the mesh is knitted. The mesh may be fabricated from any of a number of biocompatible materials, such as nylon, silicone, polyethylene, polyester, polyethylene, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

Suitable bioabsorbable synthetic materials include, without limitation, polylactic acid (PLA), polyglycolic acid (PGA), poly-L-lactic acid (PLLA), poly(amino acids), polypeptides, human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, having a single direction where the tensile strength of the material is the highest. Oriented materials may include rectus fascia and/or facia lata.

In addition to those listed above, exemplary biodegradable polymers which may be used to form the slings or, as applicable, the arms disclosed herein, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly (L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as poly(lysine), Poly(glutamic acid), gelatin and collagen; and mixtures and copolymers thereof.

The sling assemblies, including the various slings and, as applicable, the arms disclosed herein, may include an agent for release into the patient's tissues. One illustrative agent is a tissue growth factor that, when applied to the patient's tissues in a pharmaceutically acceptable amount, promotes well-organized collagenous tissue growth, such as scar tissue growth, preferably, in large quantities. According to one feature, the agent may or may not block or delay the dissolvability of the biodegradable materials. Whether or not an agent blocks or delays such dissolvability may be controlled by selecting differing methods for loading the agent onto the sling. Exemplary tissue growth factors may include natural and/or recombinant proteins for stimulating a tissue response to enhance collagenous tissue growth. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

According to another feature, the slings disclosed herein may include any suitable end portions, such as tissue dilators, anchors, and association mechanisms for associating the sling with a delivery device. Without limitation, examples of slings, sling assemblies, sling delivery devices and approaches, sling assembly-to-delivery device association mechanisms, and sling anchoring mechanisms including features with which the slings and sling assemblies of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof." Moreover, the slings disclosed herein may be adapted for use in pelvic floor repair systems and related devices and methods. Such systems include, for example, those disclosed in U.S. Pat. No. 6,197,036, entitled "Pelvic Floor Reconstruction," U.S. Pat. No. 6,691,711, entitled "Method of Correction of Urinary and Gynecological Pathologies Including Treatment of Incontinence," U.S. Pat. No. 6,884,212, entitled "Implantable Article and Method," U.S. Pat. No. 6,911,003, entitled "Transobturator Surgical Articles and Methods," U.S. patent application Ser. No. 10/840,646, entitled "Method and Apparatus for Cystocele Repair," U.S. application Ser. No. 10/834,943, entitled "Method and Apparatus for Treating Pelvic Organ Prolapse," U.S. patent application Ser. No. 10/804,718, entitled "Prolapse Repair," and U.S. patent application Ser. No. 11/115,655, entitled "Surgical Implants and Related Methods," U.S. patent application Ser. No. 11/400111, entitled "Systems, Devices, and Methods for Treating Pelvic Floor Disorders," and U.S. patent application Ser. No. 11/399913, entitled "Systems, Devices, and Methods for Sub-Urethral Support". It is intended that the scope of the invention not be limited by this detailed description.

The present disclosure contemplates all combinations of features and elements disclosed herein. For example, various embodiments of delivery devices, transfer pins, implants, implant associators, and other features described herein are interchangeable with one another, unless explicitly stated otherwise. As such, combinations of these embodiments, if not explicitly disclosed, are contemplated and within the scope of the present disclosure.

The contents of all references, patents and published patent applications cited throughout this Application, as well as their associated figures are hereby incorporated by reference in entirety.

The Figures and drawings referred to herein are not necessarily to scale; emphasis instead is generally placed upon illustrating the principles of the illustrated embodiments.

Variations, modifications, and other implementations of what is described herein will occur to those of ordinary skill without departing from the spirit and the scope of the present disclosure. Hence, many equivalents to the specific systems, methods, and other embodiments described herein exist and are considered to be within the scope of the present disclosure. For additional illustrative features that may be used with the present disclosure, including the embodiments described here, refer to the documents listed herein above and incorporated by reference in their entirety. All operative combinations between the above described illustrative embodiments and those features described in the documents incorporated by reference herein are considered to be potentially patentable embodiments of the claimed invention.

What is claimed is:

1. An implantable supportive sling assembly comprising:
   a sling having at least one through-aperture having a width;
   at least one support arm having first and second ends and at least one through-aperture on the first end, wherein the first end of the support arm has a width greater than a width of the second end, and wherein the width of the first end of the support arm is greater than the width of the through-aperture of the sling, and the width of the second end of the support arm is less than the width of the through-aperture of the sling; and
   wherein the second end of the at least one support arm is adapted to fit through the at least one through-aperture of the sling and through the at least one through-aperture of the first end of the support arm to secure the at least one support arm to the sling.

2. The sling assembly of claim 1, further comprising at least one anchor attached to the at least one support arm.

3. The sling assembly of claim 2, wherein the anchor is one or more of a soft tissue anchor and a bone anchor.

4. The sling assembly of claim 1, wherein the through-aperture of the sling includes at least one of a slot, a loop, and a ring.

5. The sling assembly of claim 4, wherein the at least one slot, loop, or ring is attached to a portion of the sling.

6. The sling assembly of claim 4, wherein the at least one slot, loop, or ring is inserted within the sling.

7. The sling assembly of claim 1, wherein the sling has a shape comprising at least one of square, rectangular, trapezoidal, quadrilateral, triangular, circular, elliptical, and polygonal.

8. The sling assembly of claim 1, wherein the at least one support arm includes two support arms.

9. The sling assembly of claim 8, wherein the sling has two through-apertures, and each support arm has a corresponding sling through-aperture.

10. The sling assembly of claim 9, wherein the sling has a rectangular shape and two through-apertures, with one through-aperture located at each end of the rectangular sling.

11. The sling assembly of claim 1, wherein the at least one support arm includes four support arms.

12. The sling of claim 11, wherein the sling has four through-apertures, and each support arm has a corresponding sling through-aperture.

13. The sling assembly of claim 12, wherein the sling has a quadrilateral shape with a through-aperture located in each corner of the sling.

14. The sling assembly of claim 1, wherein the at least one support arm includes at least two support arms, and at least two support arms correspond to a sling through-aperture.

15. The sling assembly of claim 1, wherein the sling is a mesh sling.

16. The sling assembly of claim 1, wherein the sling is a woven sling.

17. The sling assembly of claim 1, wherein the at least one support arm is a mesh arm.

18. The sling assembly of claim 1, wherein the at least one support arm includes an elastic member.

19. A method of repairing pelvic floor defects, comprising:
    providing a sling having a first through-aperture having a width, providing a support arm having first and second ends and having a second through-aperture on the first end, wherein the first end of the support arm has a width greater than a width of the second end, and wherein the width of the first end of the support arm is greater than the width of the through-aperture of the sling, and the width of the second end of the support arm is less than the width of the through-aperture of the sling; and
    inserting the first end of the support arm through the first through-aperture and then through the second through-aperture, and pulling the first end of the support arm through the first and second through-apertures to secure the support arm to the sling.

20. The method of claim 19, comprising attaching an anchor to the support arm.

21. The method of claim 20, wherein the anchor is attached to the support arm before the support arm is secured to the sling.

22. The method of claim 20, wherein the anchor is attached to the support arm after the support arm is secured to the sling.

* * * * *